(12) United States Patent
Müller et al.

(10) Patent No.: US 6,441,168 B1
(45) Date of Patent: Aug. 27, 2002

(54) STABLE CRYSTALLINE SALTS OF 5-METHYLTETRAHYDROFOLIC ACID

(75) Inventors: Rudolf Müller; Rudolf Moser, both of Schaffhausen; Thomas Egger, Effretikon, all of (CH)

(73) Assignee: Eprova AG, Schaffhausen (CH)

( * ) Notice: Subject to any disclaimer, the term of this patent is extended or adjusted under 35 U.S.C. 154(b) by 0 days.

(21) Appl. No.: 09/551,405

(22) Filed: Apr. 17, 2000

(30) Foreign Application Priority Data

Apr. 15, 1999 (CH) ................................................ 695/99

(51) Int. Cl.$^7$ ........................................... C07D 475/04
(52) U.S. Cl. ....................................................... 544/258
(58) Field of Search ......................................... 544/258

(56) References Cited

U.S. PATENT DOCUMENTS

| | | | | |
|---|---|---|---|---|
| 5,006,655 A | * | 4/1991 | Muller et al. | 544/258 |
| 5,194,611 A | * | 3/1993 | Marazza et al. | 544/258 |
| 5,223,500 A | * | 6/1993 | Gennari | 514/249 |
| 5,300,505 A | | 4/1994 | Muller | 514/250 |
| 5,324,836 A | | 6/1994 | Muller | 544/258 |
| 5,332,815 A | | 7/1994 | Molera | 544/258 |
| 5,350,850 A | * | 9/1994 | Vecchi | 544/258 |
| 5,382,581 A | | 1/1995 | Marezze | 514/245 |
| 5,457,202 A | * | 10/1995 | Scheib | 544/258 |
| 5,817,659 A | | 10/1998 | Muller | 514/245 |

FOREIGN PATENT DOCUMENTS

| | | |
|---|---|---|
| DE | 2807393 | 9/1978 |
| EP | 0455013 | 11/1991 |
| EP | 0495204 | 7/1992 |
| EP | 0535710 | 4/1993 |
| EP | 0537492 | 4/1993 |
| EP | 0539987 | 5/1993 |
| EP | 0682026 | 11/1995 |
| EP | 0773221 | 5/1997 |

OTHER PUBLICATIONS

Fitzhugh Pteridines 4, 187 (1993).*
Pauling, Linus, "General Chemistry, 2nd Ed.", 1953, Freeman, San Francisco, p 22 & 41.*
Hawley, Gessner, "The Condensed Chemical Dictonary", 1977, Van Nostrand, New York, p. 240.*
Loewenthal, H.J.E. "A Guide for the Perplexed Organic Experimentalist, 2nd Ed"., John Wiley & sons, Chichester, 1992, p 145.*
Wiberg, K.B., "Laboratory Technique in Organic Chemistry", 1960, McGraw–Hill, New York, p 99.*
Derwent English abstract of EP 539 987.
Derwent English abstract of EP 682 026.

* cited by examiner

Primary Examiner—Richard L. Raymond
Assistant Examiner—Thomas C McKenzie
(74) Attorney, Agent, or Firm—Millen, White, Zelano & Branigan, P.C.

(57) ABSTRACT

This invention relates to stable crystalline salts of 5-methyl-(6R,S)-, -(6S)- and -(6R)-tetrahydrofolic acid, to methods of producing these salts and to the use thereof use as a constituent for the production of drugs or as a food additive, and to preparations containing these salts.

17 Claims, 5 Drawing Sheets

STABLE CRYSTALLINE SALTS OF 5-METHYLTETRAHYDROFOLIC ACID

FIELD OF THE INVENTION

This invention relates to crystalline salts of N-[4-[[(2-amino-1,4,5,6,7,8hexahydro-4-oxo-5-methyl-(6S)-, -(6R)- and -(6R,S)-pteridinyl)methyl]amino]benzoyl-L-glutamic acid (hereinafter called salts of 5-methyltetrahydrofolic acid), to the use thereof, and to a method of producing them.

BACKGROUND OF THE INVENTION

Tetrahydrofolates are predominantly used as 5-formyltetrahydrofolic acid and the salts thereof (leucovorin) or as 5-methyltetrahydrofolic acid and the salts thereof, for the treatment of megaloblastic folic acid anaemia, as an antidote for increasing the compatibility of folic acid antagonists, particularly of aminopterin and methotrexate in cancer therapy ("antifolate rescue"), for increasing the therapeutic effect of fluorinated pyrimidines and for the treatment of autoimmune diseases such as psoriasis and rheumatoid arthritis, for increasing the compatibility of certain antiparasitic formulations, for instance trimethoprim-sulfamethoxazole, and for reducing the toxicity of dideazatetrahydrofolates in chemotherapy. 5-methyltetrahydrofolic acid is used in particular as a drug and as a food additive, as a vitamin preparation, for the prevention of neural tube defects, for the treatment of depressive illnesses, and for influencing the homocysteine level.

5-methyltetrahydrofolic acid and salts thereof are extremely unstable, and in particular are highly susceptible to oxidation [see also A. L. Fitzhugh, Pteridines 4 (4), 187–191 (1993) in this respect] and are therefore difficult to produce at a level of purity which is acceptable for a pharmaceutical active ingredient or a food additive.

Various methods, such as excluding oxygen as completely as possible or the addition of antioxidants such as ascorbic acid or reduced L-glutathione, have been employed in order to overcome the instability of 5-methyltetrahydrofolic acid. However, it is scarcely possible completely to exclude oxygen during use, and even then this is only possible at very considerable cost, and the addition of antioxidants is likewise not always possible. Accordingly, it has not been possible hitherto to identify a commercially feasible method which is suitable for the production of salts of 5-methyltetrahydrofolic acid which are satisfactorily stable and which are of high purity.

SUMMARY OF THE INVENTION

Surprisingly, it has now been found that salts of 5-methyltetrahydrofolic acid which exhibit high chemical purity and excellent stability can be obtained by crystallising the corresponding salt from a polar medium after subjecting the solution to thermal treatment at a temperature above 60° C. The highly crystalline salts of 5-methyl-tetrahydrofolic acid which are thus obtained are stable at room temperature, practically without-limitation They are suitable as a constituent or as a starting material for the production of drug forms or food additives.

Accordingly, the present invention relates to crystalline salts of 5-methyltetrahydrofolic acid. Alkaline earth salts, particularly the calcium salt, are preferably used as the salts of 5-methyltetrahydrofolic acid for crystallisation. These crystalline salts of 5-methyltetrahydrofolic acid exhibit a purity, which has never been achieved hitherto, of >98%, together with a stability, with respect to the initial value thereof and which has never been achieved hitherto, of >98% after storage for 6 months in air at 25° C. and 60% relative atmospheric humidity. The crystalline calcium salts of 5-methyl-(6S)-tetrahydrofolic acid exist in four different crystalline modifications (Type I, Type II, Type III and Type IV) and exhibit sharp bands when subjected to X-ray powder diffraction measurements (see Table 1 to Table 4 in this respect). Selected 2 theta values for the different crystalline modifications are 6.5, 13.3, 16.8 and 20.1 (Type I); 5.3, 6.9, 18.7 and 21.1 (Type II); 6.8, 10.2, 15.4 and 22.5 (Type III); and 6.6, 15.9, 20.2 and 22.5 (Type IV). Crystalline calcium salts of 5-methyltetrahydrofolic acid have a content of water of crystallisation of at least 1 equivalent of water per 1 equivalent of 5-methyltetrahydrofolic acid. Thus the Type I modification typically contains $\geq 3$ equivalents of water, the Type II modification typically contains $\leq 2$ equivalents water and the Type III and Type IV modifications typically contain $\leq 5$ equivalents of water.

Other Salts of 5-methyl-(6R)-tetrahydrofolic acid and salts of 5-methyl-(6R,S)-tetrahydrofolic acid can likewise be obtained in highly crystalline form.

The present invention further relates to a method of producing highly crystalline salts of 5-methyltetrahydrofolic acid, which is characterised in that the corresponding salt of 5-methyltetrahydrofolic acid is crystallised. In this method, crystallisation of salts of 5-methyltetrahydrofolic acid is effected from a polar medium after thermal treatment at a temperature above 60° C., particularly above 85° C.

Substances which are particularly suitable as the polar medium include water or a mixture of water and an organic solvent which is miscible with water, such as watersoluble alcohols, e.g. methanol, ethanol, n-propanol, iso-propanol or ethylene glycol, a low molecular weight aliphatic water-soluble carboxylic acid e.g. formic acid, acetic acid or lactic acid, or water-soluble amides e.g. formamide, dimethylformamide, dimethylacetamide, 1-methylpyrrolidone, 2-methylpyrrolidone or 2-piperidinone. There are no particular restrictions with regard to the type of solvent used and with regard to the mixture ratio, since crystalline salts of 5-methyltetrahydrofolic acid generally exhibit solubilities which are lower than those of the corresponding amorphous forms.

Crystallisation is preferably effected from solutions. It is also possible to effect crystallisation from a suspension, however.

Aside from calcium salts, still further salts of 5-methyl-(6R,S) or (6R) or (6S) hydrofolic acids include but are not limited to other alkaline earth salts, for example, magnesium can be obtained in highly crystalline forms.

The different crystalline modifications can be converted into one another by further thermal treatments at temperatures above 60° C. Thus Type I, which is produced by crystallisation from a polar medium after thermal treatment at a temperature above 60° C., can be converted into Type II by drying sufficiently, e.g. under vacuum at 70° C., can be converted into Type III by sufficient thermal treatment at a temperature above 90° C., and can be converted into Type IV by sufficient thermal treatment at a temperature above 95° C.

Type II can be converted into Type 1 again by adding water to the crystals, e.g. by treatment with water in a humidity cabinet at 90° C.

Crystallisation of the salts of 5-methyltetrahydrofolic acid occurs spontaneously or is effected by seeding with the corresponding crystalline salt of 5-methyltetrahydrofolic acid.

A suitable, preferred starting material for crystallisation is pure, amorphous or crystalline 5-methyl(6S)- or -(6R)-tetrahydrofolic acid. Racemic 5-methyl-(6R,S) tetrahydrofolic acid can also be used, however, as can enriched 5-methyl-(6S)-, -(6R)- or -(6R,S)-tetrahydrofolic acid.

By using amorphous or partly crystalline, optically pure 5-methyltetrahydrofolic acid or salts thereof as the starting material for crystallisation, essentially crystalline salts of 5-methyltetrahydrofolic acid of a purity which has never been achieved hitherto, together with a stability which has never been achieved hitherto, are obtained by the method described here.

The present invention also relates to the use of highly crystalline salts of 5-methyltetrahydrofolic acid as a constituent for the production of drugs or food additive substances or for the production of other tetrahydrofolic acid derivatives, since, on account of their excellent stability in solid form, crystalline salts of 5-methyltetrahydrofolic acid are of a very good quality which remains constant with time, practically without limits. The present invention also relates to preparations containing highly crystalline salts of 5-methyltetrahydrofolic acid. These preparations are produced by known methods. They are employed analogously to the use of known substances from the field of tetrahydrofolates, such as 5-formyltetrahydrofolic acid (leucovorin) for example.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

EXAMPLES WHICH ILLUSTRATE THE INVENTION

The content of 5-methyltetrahydrofolic acid salt which is quoted in the examples was s determined by HPLC in each case and is given as % area. The water content was determined by a Karl Fischer method.

Example 1

Stabilities

In order to determine the stabilities of the crystalline salts of 5-methyltetrahydrofolic acid, the substances were stored, together with comparison specimens, in air at 25° C. and at 60% relative humidity. The content of 5-methyltetrahydrofolic acid salt remaining was measured at periodic intervals and is given by comparison with the initial value.

|  | Time of storage in months | | | | | |
|---|---|---|---|---|---|---|
|  | 0 | 3 | 6 | 12 | 18 | 88 |
| Crystalline calcium salt of 5-methyl-(6S)-tetrahydrofolic acid | 100% | 98.6% | 98.7% | 99.1% | 99.0% | 97.8% |
| Amorphous calcium salt of 5-methyl-(6S)-tetrahydrofolic acid | 100% | | 84.2% | | | |

The crystalline salts of 5-methyltetrahydrofolic acid were still very light in colour even after an extended period of storage. In contrast thereto, the amorphous samples exhibited considerable discoloration, which occurred very rapidly.

Example 2

X-ray Powder Plots

X-ray powder plots (diffraction spectra) of these substances were recorded in order to characterise the structural properties (crystalline modifications) of the crystalline salts of 5-methyltetrahydrofolic acid.

The crystalline salts of 5-methyltetrahydrofolic acid exhibited spectra of good resolution, with sharp bands and low background effects. The spectra indicated highly crystalline constituents.

Figure 1:
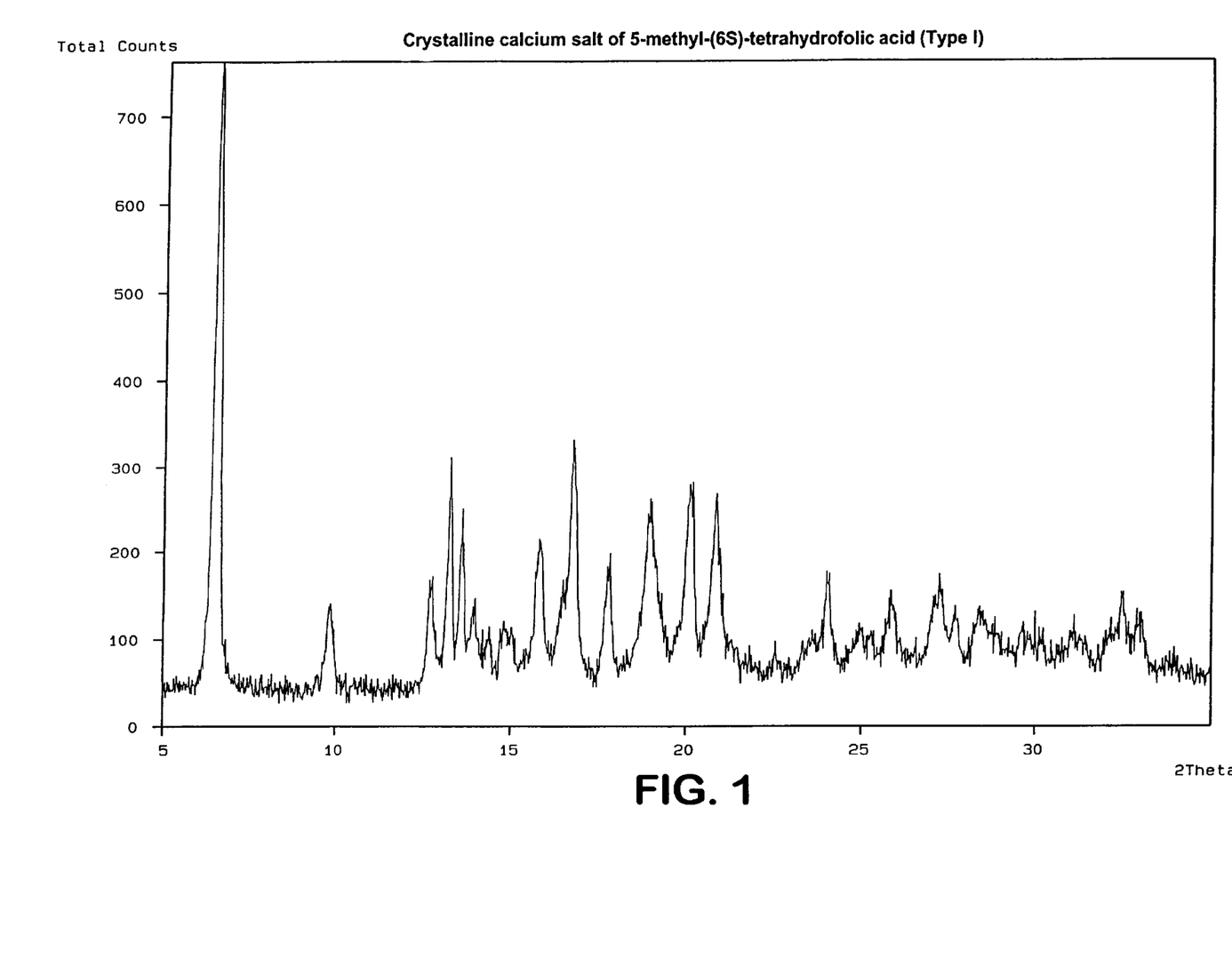
FIGS. 1–4 are self-explanatory X-ray powder diffraction diagrams of the 4 crystalline modifications of the calcium salts of the invention.
Figure 2:
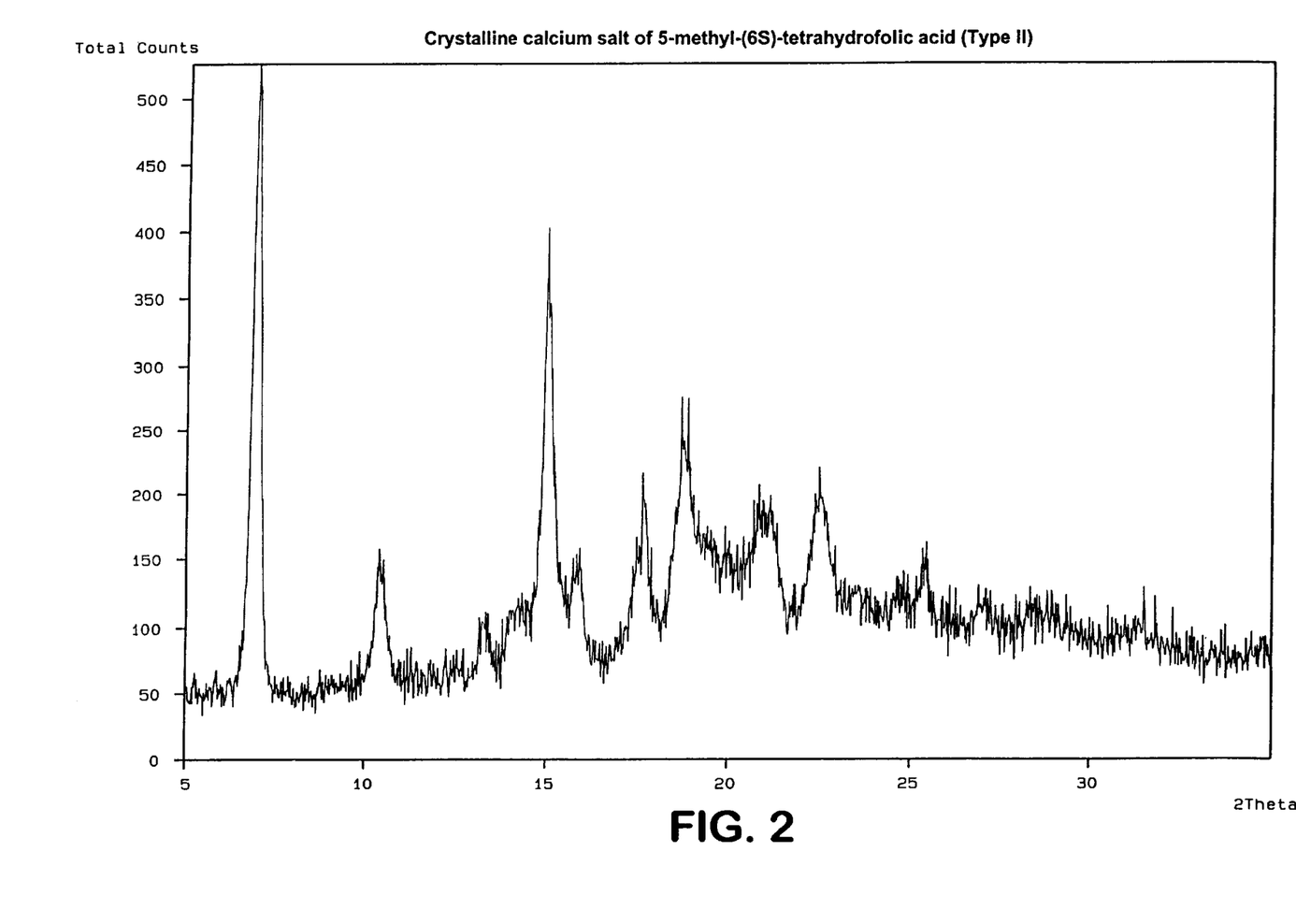
Figure 3:
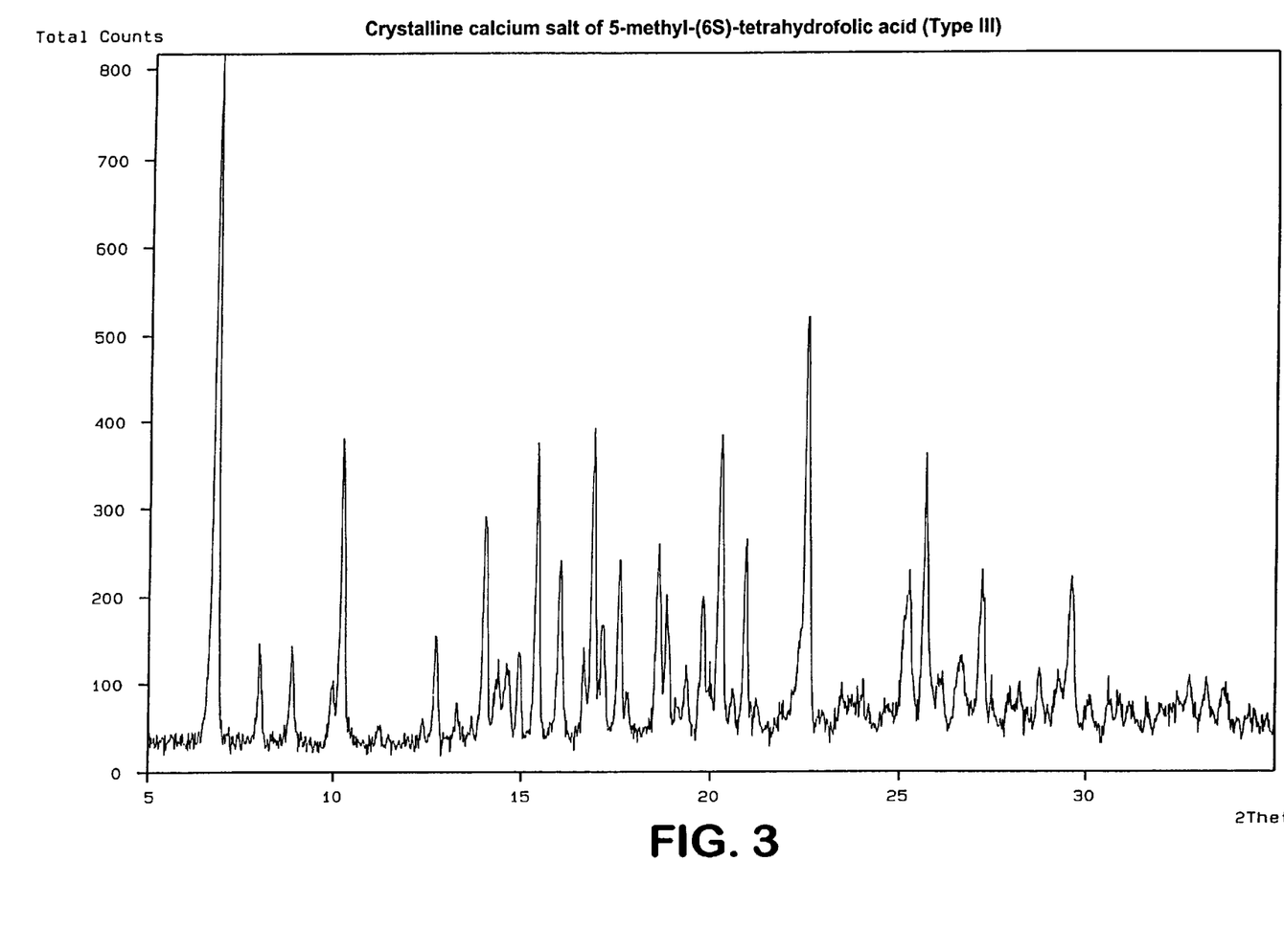
Figure 4:
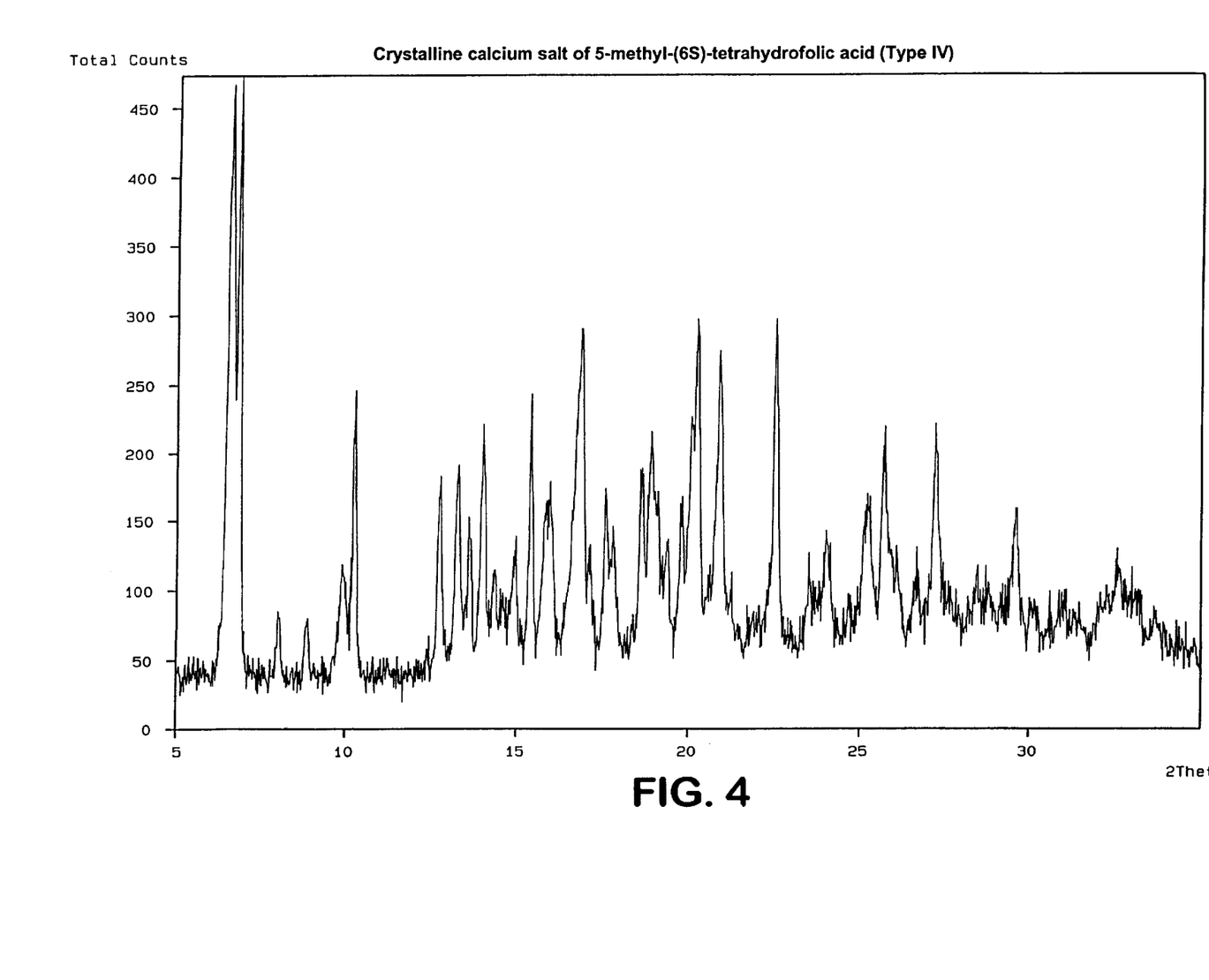
Figure 5:
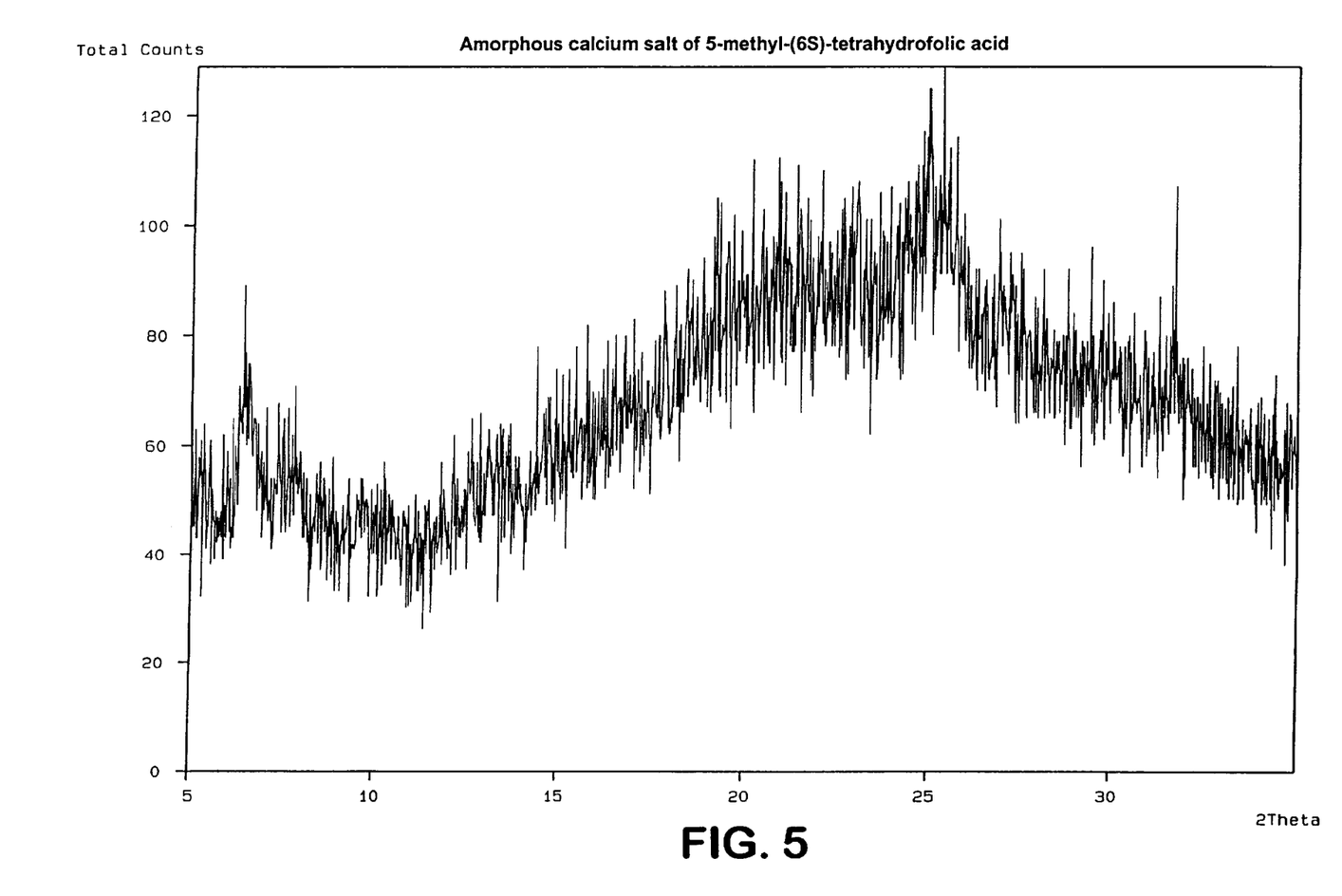
FIG. 5 is a diagram of the amorphous salt.

Examples of spectra are illustrated in FIG. 1 (Type I), FIG. 2 (Type II), FIG. 3 (Type III) and FIG. 4 (Type IV), and are presented in Table 1 (Type I), Table 2 (Type II), Table 3 (Type III) and Table 4 (Type IV). For comparison, a spectrum of an amorphous sample was also recorded under analogous conditions and is presented as FIG. 5 (amorphous).

Selected 2 theta values for the different crystalline modifications of the crystalline calcium salt of 5-methyl-(6S)-tetrahydrofolic acid are listed below:

| Type | Selected 2 theta values |
|---|---|
| Type I | 6.5, 13.3, 16.8 and 20.1 |
| Type II | 5.3, 6.9, 18.7 and 21.1 |
| Type III | 6.8, 10.2, 15.4 and 22.5 |
| Type IV | 6.6, 15.9, 20.2 and 22.5 |

Example 3

Solubilities

The solubility of the crystalline calcium salt of 5-methyl-(6S)-tetrahydrofolic acid is given in the following Table:

|  | Solubility at 20° C. in | |
|---|---|---|
| Type | 0.9% NaCl | water |
| Type I | 1.6% | 1.1% |
| Type II | 5.8% | 3.8% |
| Type III | 1.5% | 1.0% |

Example 4

Amorphous Calcium Salt of 5-Methyl-(6S)-tetrahydrofolic Acid 7.5 g 5-methyl-(6S)-tetrahydrofolic acid were introduced into 75 ml water at room temperature whilst passing $N_2$ into the batch, and the batch was adjusted to pH 12 with aqueous 30% sodium hydroxide solution. The clear solution which was thus obtained was adjusted to pH 7.5 with 37% hydrochloric acid and was treated with a solution of 7.15 g calcium chloride $6H_2O$ in 11.7 ml water. The white suspension which was formed was stirred for 5 hours and was then filtered under suction at room temperature. The solid was washed with water and was dried under vacuum at 45° C.

5.8 g of a white, amorphous calcium salt of 5-methyl-(6S)-tetrahydrofolic acid were obtained, which had a content of 98.0% and a 6S fraction corresponding to 99.6%.

Even after treating this substance at 60° C. in a humidity cabinet, no crystalline fractions could be determined either under a polarising microscope or by X-ray diffraction measurements.

Example 5

Crystalline Calcium Salt of 5-Methyl-(6 R,S)-tetrahydrofolic Acid 70 g 5-methyl-(6R, S)-tetrahydrofolic acid were placed in a vessel in 780 ml water and the batch was adjusted to pH 7.5 with 45.2 g of 30% NaOH. The clear, slightly reddish solution was treated with a solution of 62.7 g calcium chloride $6H_2O$ in 140 ml water, and the solid was filtered off and washed with a little water. The crude product which was thus obtained was suspended in water and treated at 90° C. for 24 hours.

74.0 g of a white, crystalline calcium salt of 5-methyl-(6R,S)-tetrahydrofolic acid was obtained, with a content of 99.1%.

Example 6

Crystalline Calcium Salt of 5-Methyl-(6R)-tetrahydrofolic Acid 16.5 g 5-methyl-(6R)-tetrahydrofolic acid were placed in a vessel in 100 ml water at 92° C. with 50 g calcium chloride $6H_2O$. The clear, slightly yellowish suspension was stirred for 10 minutes at 91° C., and the solid was filtered off, washed with a little water and dried at 35° C. under vacuum.

15.4 g of a light beige crystalline calcium salt of 5-methyl-(6R)-tetrahydrofolic acid were obtained, with a content of 97.9% and a water content of 7.8%.

Example 7

Type I 130 kg water were placed in a vessel and 12.8 kg 5-methyl-(6S)-tetrahydrofolic acid were introduced. The pH was adjusted to 11.6 with about 9.1 kg of 30% NaOH, and was then adjusted to 7.6 with about 1.9 kg of 37% hydrochloric acid. A suspension containing 0.3 kg carbon and 0.3 kg Cellflock was added to the clear solution. The solid was filtered off and washed with 13 litres of water. The filtrate was treated with a solution containing 8.3 kg calcium chloride $2H_2O$, heated to 90° C. and stirred for 30 minutes. The product was filtered hot and was washed with 2×20 kg water. The moist crude product which was thus obtained was slurried in 115 litres of water, heated to 90° C., immediately filtered hot, washed with 2×20 kg water, and dried at 40° C. under vacuum.

11.6 kg of a white, crystalline calcium salt of 5-methyl-(6S)-tetrahydrofolic acid (Type I) were obtained, which had a purity of 99.0% and a water content of 14.5%.

Example 8

Type I 1600 ml water were placed in a vessel and 194 g 5-methyl-(6S)-tetrahydrofolic acid were introduced. The pH was adjusted to 7.0 with about 80 ml of 30% NaOH. A suspension containing 20 g carbon and 20 g Cellflock in 190 ml water was added to the clear solution. The solid was filtered off and washed with water. The filtrate was treated with 950 ml of a 5.5 M calcium chloride solution, heated to 90° C. and stirred for 60 minutes. The product was filtered hot, washed with water, and dried at 45° C. under vacuum.

156.2 g of a white, crystalline calcium salt of 5-methyl-(6S)-tetrahydrofolic acid (Type I) were obtained, with a purity of 99.7% and a 6S fraction of 99.9%.

Example 9

Type 1 and Conversion Into Type II 554 g water were placed in a vessel and 53.1 g 5-methyl-(6S)-tetrahydrofolic acid were introduced. The pH was adjusted to 7.5 with 30% NaOH. 1.3 g carbon, 1.3 g Cellflock and 19.5 g water were added to the clear solution. The suspension was filtered and the solid was washed with 55 ml water. The filtrate was treated with a solution of 52.0 g calcium chloride $6H_2O$ in 84.6 g water, and was heated to 90° C. and seeded with 100 mg of the crystalline calcium salt of 5-methyltetrahydrofolic acid. After crystallisation had occurred, the product was filtered hot at 90° C. and was washed with 2×103 g water. The moist crude product which was thus obtained was slurried in 480 ml water, heated to 90° C., immediately filtered hot, washed as above, and dried at 45° C. under vacuum.

47.5 g of a white, crystalline calcium salt of 5-methyl-(6S)-tetrahydrofolic acid (Type I) were obtained, with a purity of 98.8% and a water content of 12.2%.

This Type I modification could be converted into the Type II modification with a water content of 5.0% by drying it at 70° C. under vacuum for 30 minutes.

Example 10

Type III 15.8 9 of the calcium salt of 5-methyl-(6S)-tetrahydrofolic acid were heated to 95° C. in 140 ml water whilst passing $N_2$ through the batch. After 30 minutes at 95° C. the white suspension was filtered hot under suction, and the solid was washed with water and dried at 35° C. under vacuum.

14.0 g of a white, crystalline calcium salt of 5-methyl-(6S)-tetrahydrofolic acid (Type III) was obtained, with a content of 98.9% and a 6S fraction of 99.9%.

Example 11

Type IV 20.0 g of the calcium salt of 5-methyl-(6S)-tetrahydrofolic acid were heated to 100° C. in 180 ml water whilst passing $N_2$ through the batch. After 30 minutes at 100° C. the white suspension was filtered hot under suction, and the solid was washed with water and dried at 25° C. under vacuum.

16.9 g of a white, crystalline calcium salt of 5-methyl-(6S)-tetrahydrofolic acid (Type IV) were obtained, with a content of 98.3% and a water content of 9.9%.

By drying it at 65° C. under vacuum, the water content of this product could be reduced to 5.5% without a different crystalline modification being obtained in the course of this procedure.

Examples of Uses of the Crystalline Material
(a) As constituent for the production of drugs:
Beside the well known uses of 5-formyltetrahydrofolic acid previously described, reference is invited to U.S. Ser. No. 09/095,572 for pharmaceutical preparations including pharmaceutically acceptable excipients, as well as dosage ranges of 5-methyltetrahydrofolic acid.
(b) As food additive:
The range of possible applications as food additive is very wide (from single preparations to multivitamin preparations and grain to breakfast foods). Please refer to e.g. WO 97/27764, SAMSF/Bailey et al., for examples (e.g. examples 1, 2, 6, 8 and 9 all contain formulas with 5-methyltetrahydrofolic acid).
(c) For the production of other tetrahydrofolic acid derivatives:
Under "other tetrahydrofolic acid derivatives", other salts of 5-methyltetrahydrofolic acid and the free acid itself are especially included.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding Swiss application 695/99, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

TABLE 1

Crystalline calcium salt of 5-methyl-(6S)-tetrahydrofolic acid (Type I)

Diffractometer : Transmission
Monochromator : Curved Ge (111)
Wavelength : 1.540598 Cu
Detector : Linear PSD
Scan Mode : Debye-Scherrer/Moving PSD/Fixed omega 2Theta scan
! Peak search parameters : Expected halfwidth : .150
!                              Significance level : 2.5
!                              Peak height level : 10
Peaklist [Range 1 : 2Theta = 5.000 34.980 .020 Imax = 765]

| ! | D | 2Theta | I (rel) | I (abs) | FWHM | h | k | l |
|---|---|---|---|---|---|---|---|---|
| | 13.474630 | 6.5544 | 100.0 | 755 | .2200 | | | |
| | 8.979750 | 9.8420 | 18.5 | 140 | .1600 | | | |
| | 6.936035 | 12.7526 | 20.3 | 153 | .1600 | | | |
| | 6.662427 | 13.2786 | 38.3 | 289 | .0800 | | | |
| | 6.497896 | 13.6164 | 29.4 | 222 | .1200 | | | |
| | 6.323596 | 13.9935 | 18.8 | 142 | .0200 | | | |
| | 6.148863 | 14.3933 | 14.0 | 106 | .0400 | | | |
| | 5.966675 | 14.8352 | 15.5 | 117 | .1200 | | | |
| | 5.593548 | 15.8309 | 27.5 | 208 | .2200 | | | |
| | 5.368022 | 16.5006 | 19.7 | 149 | .1127 | | | |
| | 5.282104 | 16.7709 | 42.5 | 321 | .2000 | | | |
| | 4.977751 | 17.8044 | 23.6 | 178 | .1800 | | | |
| | 4.672452 | 18.9782 | 32.7 | 247 | .2800 | | | |
| | 4.411916 | 20.1102 | 34.8 | 263 | .0800 | | | |

TABLE 1-continued

Crystalline calcium salt of 5-methyl-(6S)-tetrahydrofolic acid (Type I)

Diffractometer : Transmission
Monochromator : Curved Ge (111)
Wavelength : 1.540598 Cu
Detector : Linear PSD
Scan Mode : Debye-Scherrer/Moving PSD/Fixed omega 2Theta scan
! Peak search parameters : Expected halfwidth : .150
!                              Significance level : 2.5
!                              Peak height level : 10
Peaklist [Range 1 : 2Theta = 5.000 34.980 .020 Imax = 765]

| ! | D | 2Theta | I (rel) | I (abs) | FWHM | h | k | l |
|---|---|---|---|---|---|---|---|---|
| | 4.257688 | 20.8467 | 34.2 | 258 | .2600 | | | |
| | 3.761157 | 23.6360 | 13.3 | 100 | .0400 | | | |
| | 3.699455 | 24.0361 | 22.3 | 168 | .1400 | | | |
| | 3.558431 | 25.0037 | 14.8 | 112 | .1000 | | | |
| | 3.439070 | 25.8864 | 21.0 | 159 | .1400 | | | |
| | 3.272550 | 27.2283 | 22.1 | 167 | .2800 | | | |
| | 3.218939 | 27.6907 | 17.0 | 129 | .1400 | | | |
| | 3.140884 | 28.3931 | 17.2 | 130 | .0800 | | | |
| | 3.013536 | 29.6198 | 13.9 | 105 | .1000 | | | |
| | 2.873482 | 31.0991 | 15.1 | 114 | .0200 | | | |
| | 2.782802 | 32.1395 | 16.6 | 125 | .0200 | | | |
| | 2.754830 | 32.4748 | 20.2 | 152 | .0600 | | | |
| | 2.713309 | 32.9858 | 15.4 | 116 | .1127 | | | |

TABLE 2

Crystalline calcium salt of 5-methyl-(6S)-tetrahydrofolic acid (Type II)

Diffractometer : Transmission
Monochromator : Curved Ge (111)
Wavelength : 1.540598 Cu
Detector : Linear PSD
Scan Mode : Debye-Scherrer/Moving PSD/Fixed omega 2Theta scan
! Peak search parameters : Expected halfwidth : .150
!                              Significance level : 2.5
!                              Peak height level : 10
Peaklist [Range 1 : 2Theta = 5.000 34.980 .020 Imax = 526]

| ! | D | 2Theta | I (rel) | I (abs) | FWHM | h | k | l |
|---|---|---|---|---|---|---|---|---|
| | 12.720530 | 6.9434 | 100.0 | 517 | .2600 | | | |
| | 8.508053 | 10.3891 | 29.4 | 152 | .2400 | | | |
| | 6.631466 | 13.3409 | 19.6 | 101 | .1200 | | | |
| | 5.883504 | 15.0461 | 71.2 | 368 | .2200 | | | |
| | 5.580025 | 15.8696 | 27.8 | 144 | .0800 | | | |
| | 5.010988 | 17.6854 | 42.5 | 220 | .1400 | | | |
| | 4.730443 | 18.7434 | 53.6 | 277 | .1400 | | | |
| | 4.215807 | 21.0561 | 35.5 | 184 | .0400 | | | |
| | 3.943879 | 22.5263 | 38.8 | 201 | .3600 | | | |
| | 3.581969 | 24.8368 | 24.8 | 128 | .0200 | | | |
| | 3.493985 | 25.4726 | 29.6 | 153 | .0400 | | | |
| | 3.309171 | 26.9212 | 22.7 | 117 | .0200 | | | |

TABLE 3

Crystalline calcium salt of
5-methyl-(6S)-tetrahydrofolic acid (Type III)

Diffractometer : Transmission
Monochromator : Curved Ge (111)
Wavelength : 1.540598 Cu
Detector : Linear PSD
Scan Mode : Debye-Scherrer/Moving PSD/Fixed omega 2Theta scan
! Peak search parameters : Expected halfwidth : .150
!                              Significance level : 2.5
!                              Peak height level : 10
Peaklist [Range 1 : 2Theta = 5.000 34.980 .020 Imax = 817]

| D | 2Theta | I (rel) | I (abs) | FWHM | h | k | l |
|---|---|---|---|---|---|---|---|
| 12.933490 | 6.8289 | 100.0 | 786 | .1200 | | | |
| 11.036740 | 8.0043 | 18.9 | 149 | .0400 | | | |
| 9.945525 | 8.8842 | 18.4 | 145 | .1000 | | | |
| 8.877709 | 9.9554 | 12.4 | 98 | .0796 | | | |
| 8.640580 | 10.2293 | 49.6 | 390 | .1000 | | | |
| 7.873330 | 11.2292 | 6.4 | 50 | .1000 | | | |
| 7.144004 | 12.3799 | 7.6 | 59 | .0800 | | | |
| 6.948557 | 12.7295 | 20.3 | 159 | .1000 | | | |
| 6.659956 | 13.2835 | 10.1 | 80 | .0400 | | | |
| 6.466239 | 13.6834 | 7.6 | 60 | .0200 | | | |
| 6.305060 | 14.0349 | 37.6 | 296 | .1000 | | | |
| 6.154434 | 14.3802 | 16.4 | 129 | .0400 | | | |
| 6.057193 | 14.6123 | 15.3 | 121 | .0600 | | | |
| 5.920458 | 14.9517 | 17.6 | 139 | .1000 | | | |
| 5.738533 | 15.4285 | 48.9 | 385 | .1000 | | | |
| 5.530167 | 16.0136 | 30.3 | 238 | .1000 | | | |
| 5.322477 | 16.6428 | 18.1 | 143 | .0600 | | | |
| 5.245302 | 16.8894 | 47.4 | 372 | .0800 | | | |
| 5.154604 | 17.1888 | 20.9 | 164 | .0796 | | | |
| 5.038273 | 17.5888 | 30.8 | 242 | .1000 | | | |
| 4.980502 | 17.7945 | 10.7 | 84 | .0796 | | | |
| 4.759336 | 18.6286 | 31.6 | 248 | .1200 | | | |
| 4.702846 | 18.8544 | 24.3 | 191 | .0796 | | | |
| 4.575841 | 19.3827 | 15.6 | 122 | .0800 | | | |
| 4.478961 | 19.8061 | 25.9 | 204 | .1000 | | | |
| 4.377158 | 20.2716 | 48.1 | 378 | .1000 | | | |
| 4.309006 | 20.5957 | 11.9 | 93 | .0796 | | | |
| 4.242777 | 20.9207 | 31.3 | 246 | .0800 | | | |
| 4.051441 | 21.9207 | 10.3 | 81 | .0200 | | | |
| 3.940356 | 22.5467 | 67.8 | 533 | .1200 | | | |
| 3.782452 | 23.5010 | 12.4 | 98 | .0400 | | | |
| 3.609291 | 24.6458 | 9.5 | 75 | .0200 | | | |
| 3.523157 | 25.2582 | 27.0 | 212 | .2000 | | | |
| 3.460874 | 25.7205 | 43.4 | 341 | .0800 | | | |
| 3.408545 | 26.1223 | 12.4 | 98 | .0796 | | | |
| 3.341048 | 26.6596 | 16.1 | 127 | .2000 | | | |
| 3.273575 | 27.2196 | 28.4 | 223 | .1400 | | | |
| 3.188038 | 27.9645 | 12.6 | 99 | .0200 | | | |
| 3.160110 | 28.2168 | 12.5 | 98 | .0400 | | | |
| 3.103472 | 28.7427 | 15.0 | 118 | .0800 | | | |
| 3.052658 | 29.2317 | 13.9 | 109 | .0600 | | | |
| 3.017419 | 29.5808 | 27.7 | 218 | .1400 | | | |
| 2.970195 | 30.0621 | 10.6 | 83 | .1200 | | | |
| 2.921067 | 30.5800 | 13.9 | 109 | .0200 | | | |
| 2.899222 | 30.8161 | 9.6 | 76 | .0796 | | | |
| 2.870572 | 31.1314 | 9.6 | 75 | .0400 | | | |
| 2.830661 | 31.5817 | 11.0 | 86 | .0200 | | | |
| 2.758126 | 32.4349 | 11.3 | 89 | .0400 | | | |
| 2.733265 | 32.7382 | 13.2 | 104 | .0600 | | | |
| 2.695836 | 33.2058 | 13.7 | 108 | .0800 | | | |
| 2.660160 | 33.6643 | 11.7 | 92 | .1000 | | | |
| 2.609572 | 34.3369 | 9.2 | 72 | .0200 | | | |

TABLE 4

Crystalline calcium salt of
5-methyl-(6S)-tetrahydrofolic acid (Type IV)

| | |
|---|---|
| Diffractometer | : Transmission |
| Monochromator | : Curved Ge (111) |
| Wavelength | : 1.540598 Cu |
| Detector | : Linear PSD |
| Scan Mode | : Debye-Scherrer/Moving PSD/Fixed omega 2Theta scan |
| ! Peak search parameters | : Expected halfwidth : .150 |
| ! | Significance level : 2.5 |
| ! | Peak height level : 10 |

Peaklist [Range 1 : 2Theta = 5.000 34.980 .020 Imax = 473]

| D | 2Theta | I (rel) | I (abs) | FWHM | h | k | l |
|---|---|---|---|---|---|---|---|
| 13.398610 | 6.5916 | 97.7 | 446 | .1600 | | | |
| 12.930100 | 6.8307 | 100.0 | 457 | .0915 | | | |
| 11.033220 | 8.0069 | 19.2 | 88 | .0800 | | | |
| 9.952926 | 8.8776 | 16.7 | 76 | .1200 | | | |
| 8.912272 | 9.9167 | 25.5 | 116 | .1600 | | | |

TABLE 4-continued

Crystalline calcium salt of
5-methyl-(6S)-tetrahydrofolic acid (Type IV)

| | |
|---|---|
| Diffractometer | : Transmission |
| Monochromator | : Curved Ge (111) |
| Wavelength | : 1.540598 Cu |
| Detector | : Linear PSD |
| Scan Mode | : Debye-Scherrer/Moving PSD/Fixed omega |
| 2Theta scan | |
| ! Peak search parameters | : Expected halfwidth : .150 |
| ! | Significance level : 2.5 |
| ! | Peak height level : 10 |

Peaklist [Range 1 : 2Theta = 5.000 34.980 .020 Imax = 473]

| D | 2Theta | I (rel) | I (abs) | FWHM | h | k | l |
|---|---|---|---|---|---|---|---|
| 8.626970 | 10.2455 | 48.9 | 223 | .0800 | | | |
| 6.931997 | 12.7600 | 37.4 | 171 | .1000 | | | |
| 6.651761 | 13.3000 | 39.7 | 181 | .1200 | | | |
| 6.499623 | 13.6127 | 32.8 | 150 | .0800 | | | |
| 6.309299 | 14.0254 | 47.0 | 215 | .1600 | | | |
| 6.161306 | 14.3641 | 25.1 | 115 | .1200 | | | |
| 5.917463 | 14.9593 | 27.0 | 124 | .1000 | | | |
| 5.736254 | 15.4347 | 49.8 | 227 | .0800 | | | |
| 5.544314 | 15.9724 | 36.7 | 168 | .1600 | | | |
| 5.255854 | 16.8553 | 62.1 | 284 | .2400 | | | |
| 5.172075 | 17.1303 | 29.5 | 135 | .0915 | | | |
| 5.035719 | 17.5978 | 37.0 | 169 | .1200 | | | |
| 4.978813 | 17.8006 | 31.3 | 143 | .0400 | | | |
| 4.758441 | 18.6321 | 40.7 | 186 | .1000 | | | |
| 4.688853 | 18.9112 | 46.0 | 210 | .0915 | | | |
| 4.577465 | 19.3757 | 29.5 | 135 | .0915 | | | |
| 4.479376 | 19.8043 | 35.5 | 162 | .1000 | | | |
| 4.383704 | 20.2410 | 63.6 | 290 | .1200 | | | |
| 4.246196 | 20.9037 | 59.5 | 272 | .1400 | | | |
| 4.088125 | 21.7216 | 19.7 | 90 | .0200 | | | |
| 3.941748 | 22.5386 | 62.9 | 288 | .1400 | | | |
| 3.778991 | 23.5229 | 27.9 | 128 | .0400 | | | |
| 3.696576 | 24.0551 | 30.5 | 139 | .1000 | | | |
| 3.523769 | 25.2537 | 35.6 | 163 | .2400 | | | |
| 3.459683 | 25.7295 | 44.7 | 204 | .0800 | | | |
| 3.338511 | 26.6803 | 28.7 | 131 | .0200 | | | |
| 3.273450 | 27.2206 | 45.5 | 208 | .1000 | | | |
| 3.135320 | 28.4446 | 23.6 | 108 | .0600 | | | |
| 3.108154 | 28.6985 | 25.9 | 118 | .0200 | | | |
| 3.018687 | 29.5681 | 34.4 | 157 | .1400 | | | |
| 2.923031 | 30.5589 | 21.9 | 100 | .0200 | | | |
| 2.844431 | 31.4249 | 18.4 | 84 | .0200 | | | |
| 2.749393 | 32.5408 | 28.5 | 130 | .1200 | | | |
| 2.713739 | 32.9804 | 25.6 | 117 | .0200 | | | |
| 2.663207 | 33.6246 | 19.6 | 90 | .0600 | | | |
| 2.613490 | 34.2838 | 17.4 | 80 | .0200 | | | |

What is claimed is:

1. A crystalline salt of 5-methyl-(6R,S)-, -(6S)- or -(6R)-tetrahydrofolic acid said crystalline salt having a water of crystallization of at least one equivalent per equivalent of 5-methyltetrahydrofolic acid.

2. A crystalline salt according to claim 1, of 5-methyl-(6S)- or -(6R)-tetrahydrofolic acid.

3. A crystalline calcium salt according to claim 1, of 5-methyl-(6S)- and -(6R)-tetrahydrofolic acid having ≧3 equivalents of water.

4. A crystalline calcium salt of 5-methyl-(6S)-tetrahydrofolic acid with 2 theta values of 6.5, 13.3, 16.8 and 20.1 (Type I) said crystalline salt having a water of crystallization of at least one equivalent per equivalent of 5-methyltetrahydrofolic acid.

5. A crystalline calcium salt according to claim 1, of 5-methyl-(6S)-tetrahydrofolic acid with 2 theta values of 5.3, 6.9, 18.7 and 21.1 (Type II).

6. A crystalline calcium salt according to claim 1, of 5-methyl-(6S)-tetrahydrofolic acid with 2 theta values of 6.8, 10.2, 15.4 and 22.5 (Type III).

7. A crystalline calcium salt according to claim 1, of 5-methyl-(6S)-tetrahydrofolic acid with 2 theta values of 6.6, 15.9, 20.2 and 22.5(Type IV).

8. A method of producing crystalline salts of 5-methyl-(6R,S)-, -(6S)- and 5-methyl-(6R)-tetrahydrofolic acid, comprising subjecting a salt of 5-methyl-(6R,S)-, -(6S)- or -(6R)-tetrahydrofolic acid in a polar medium to a thermal treatment, at a temperature above 60° C., and thereafter crystallizing said salt from the resultant heated solution.

9. A method according to claim 8, wherein the crystallisation is effected after thermal treatment at a temperature above 85° C.

10. A method according to claim 8, wherein the crystallisation is effected from a solution.

11. A method according to claim 8, wherein the crystallisation is effected from a suspension.

12. A method according to claim 10, characterised in that crystallisation is effected from water or from a mixture of water and an organic solvent which is miscible with water.

13. A method according to claim 8, wherein said salt is an alkaline earth salt.

14. A method according to claim 8, wherein said salt is calcium.

15. A method of producing 5-methyl-(6S)-tetrahydrofolic acids with 2 theta values of 5.3, 6.9, 18.7 and 21.1 (Type II) comprising drying sufficiently 5-methyl-(6S)-tetrahydrofolic acid with 2 theta values of 6.5, 13.3, 16.8 and 20.1 (Type I).

16. A method of producing 5-methyl-(6S)-tetrahydrofolic acid with 2 theta values of 6.8, 10.2, 15.4 and 22.5 (Type III) comprising subjecting to sufficient thermal treatment at above 90° C., a crystalline calcium salt of 5-methyl-(6S)-tetrahydrofolic acid with 2 theta values of 6.5, 13.3, 16.8 and 20.1 (Type I).

17. A method of producing 5-methyl-(6S)-tetrahydrofolic acid with 2 theta values of 6.6, 15.9, 20.2, 22.5 (Type IV) comprising subjecting to sufficient thermal treatment at above 95 ° C., a crystalline calcium salt of 5-methyl-(6S)-tetrahydrofolic acid with 2 theta values of 6.5, 13.3, 16.8 and 20.1 (Type I).

* * * * *

UNITED STATES PATENT AND TRADEMARK OFFICE
CERTIFICATE OF CORRECTION

PATENT NO. : 6,441,168 B1
DATED : August 27, 2002
INVENTOR(S) : Rudolf Muller et al.

It is certified that error appears in the above-identified patent and that said Letters Patent is hereby corrected as shown below:

Column 12,
Line 4, reads "acids," should read -- acid --

Signed and Sealed this

First Day of June, 2004

JON W. DUDAS
*Acting Director of the United States Patent and Trademark Office*